US010912669B2

(12) United States Patent
Shan et al.

(10) Patent No.: US 10,912,669 B2
(45) Date of Patent: Feb. 9, 2021

(54) ELECTRIC BED

(71) Applicant: Keeson Technology Corporation Limited, Zhejiang (CN)

(72) Inventors: Huafeng Shan, Zhejiang (CN); Hui Cao, Zhejiang (CN); Qun Yu, Zhejiang (CN)

(73) Assignee: Keeson Technology Corporation Limited, Jiaxing (CN)

( * ) Notice: Subject to any disclaimer, the term of this patent is extended or adjusted under 35 U.S.C. 154(b) by 209 days.

(21) Appl. No.: 16/052,957

(22) Filed: Aug. 2, 2018

(65) Prior Publication Data

US 2018/0338624 A1 Nov. 29, 2018

Related U.S. Application Data

(63) Continuation of application No. PCT/CN2017/072417, filed on Jan. 24, 2017.

(30) Foreign Application Priority Data

Feb. 2, 2016 (CN) .......................... 2016 2 0103834

(51) Int. Cl.
*A61F 5/56* (2006.01)
*A47C 20/04* (2006.01)
(Continued)

(52) U.S. Cl.
CPC ................ *A61F 5/56* (2013.01); *A47C 20/04* (2013.01); *A47C 20/041* (2013.01); *A61B 5/002* (2013.01);
(Continued)

(58) Field of Classification Search
CPC ....... A47C 20/04; A47C 20/08; A47C 20/041; A47C 31/008; A47C 31/123; A61F 5/56;
(Continued)

(56) References Cited

U.S. PATENT DOCUMENTS 3,089,130 A * 5/1963 Wilson ...................... A61F 5/56 340/575
6,502,264 B1 * 1/2003 Clothier ............... A47C 20/041 368/12
(Continued)

FOREIGN PATENT DOCUMENTS

CN 202605093 U 12/2012
CN 103429212 A 12/2013
(Continued)

OTHER PUBLICATIONS

The First Examination Report of counterpart Australian Standard Patent Application No. 2017215679 dated Nov. 30, 2018.
(Continued)

*Primary Examiner* — David R Hare

(57) ABSTRACT

An electric bed includes: a bed body, a plurality of bed planks, a driver for driving the head bed plank to rotate, a monitoring module, a driving module and a wireless communication module. When the monitoring module detects that the user is snoring, the driving module controls the driver to drive the head bed plank to rotate to an anti-snoring position. When the symptoms of snoring weaken or stop, the driving module controls the driver to drive the head bed plank to restore to an initial position. The wireless communication module is electrically connected to the driving module. The wireless communication module is wirelessly connected to an intelligent terminal. The user sets an anti-snoring program into the intelligent terminal, and then the intelligent terminal transmits the anti-snoring program to the wireless communication module, and the wireless communication module sends an application situation of the anti-snoring function to the intelligent terminal.

8 Claims, 4 Drawing Sheets

Intelligent terminal 4
11 1 1 12 18 3 13 17 14 1a 2 15 10 2a

(51) Int. Cl.
*A61M 21/00* (2006.01)
*A61G 7/015* (2006.01)
*A61B 5/08* (2006.01)
*A61B 5/00* (2006.01)

(52) U.S. Cl.
CPC .............. *A61B 5/08* (2013.01); *A61B 5/4809* (2013.01); *A61B 5/6891* (2013.01); *A61B 5/7282* (2013.01); *A61M 21/00* (2013.01); *A61B 5/4818* (2013.01); *A61B 2562/0247* (2013.01); *A61G 7/015* (2013.01)

(58) Field of Classification Search
CPC .... A61G 7/015; A61B 5/7282; A61B 5/6891; A61B 5/002; A61B 5/08; A61B 5/7475; A61B 5/4818; A61B 5/1115; A61B 5/0205; A61B 5/4806; A61B 2562/0247
See application file for complete search history.

(56) References Cited

U.S. PATENT DOCUMENTS

| | | | | |
|---|---|---|---|---|
| 7,522,062 | B2 * | 4/2009 | Mossbeck | A61G 7/015 340/575 |
| 8,832,887 | B2 * | 9/2014 | Mossbeck | A47C 27/10 5/713 |
| 10,058,467 | B2 * | 8/2018 | Stusynski | A47C 20/041 |
| 10,529,217 | B2 * | 1/2020 | Shan | A61M 21/00 |
| 2005/0211247 | A1 | 9/2005 | Noda et al. | |
| 2010/0302044 | A1 * | 12/2010 | Chacon | A61F 5/56 340/575 |
| 2012/0138067 | A1 * | 6/2012 | Rawls-Meehan | A47C 20/041 128/845 |
| 2012/0324649 | A1 * | 12/2012 | Lin | A61F 5/56 5/613 |
| 2014/0259417 | A1 | 9/2014 | Nunn et al. | |
| 2014/0371635 | A1 | 12/2014 | Shinar et al. | |
| 2016/0066703 | A1 * | 3/2016 | Chen | A61B 5/6892 5/613 |
| 2016/0213309 | A1 * | 7/2016 | Sannholm | A61B 5/1116 |
| 2018/0071133 | A1 * | 3/2018 | Hariri | A61B 5/4818 |

FOREIGN PATENT DOCUMENTS

| | | | |
|---|---|---|---|
| CN | 104188638 | A | 12/2014 |
| JP | H07-31592 | A | 2/1995 |
| JP | H10192246 | A | 7/1998 |
| JP | 2005270627 | A | 10/2005 |
| JP | 2007222462 | A | 9/2007 |
| JP | 2009233027 | A | 10/2009 |
| JP | 2014204846 | A | 10/2014 |
| WO | 2012061406 | A2 | 5/2012 |

OTHER PUBLICATIONS

International Search Report of PCT Patent Application No. PCT/CN2017/072417 dated Mar. 3, 2017.
The extended European Search Report of counterpart European Patent Application No. 17746893.1 dated May 20, 2019.

* cited by examiner

ELECTRIC BED

CROSS-REFERENCE OF RELATED APPLICATIONS

The present application is a Continuation Application of PCT patent application No. PCT/CN2017/072417 filed on Jan. 24, 2017, which claims the Priority of Chinese patent application no. 201620103834.X filed on Feb. 2, 2016. All the above are hereby incorporated by reference.

FIELD OF TECHNOLOGY

The present application relates to an electric bed, in particular to an electric bed with intelligent anti-snoring function.

BACKGROUND TECHNOLOGY

Snoring at night can bring a variety of hazards. For example, snoring may disturb others' sleeping, and may even affect personal health of snorers. Common potential risks include hypoxia, apnea, hormonal dysfunction, and cardiovascular disease.

Therefore, an anti-snoring electric bed has been invented. For example, patent document CN201220212034 discloses an electric bed having a mechanical arm. The electric bed has a sound collector for collecting a breathing sound and a snoring sound when a user sleeps, and a smart sensor for analyzing and processing the sounds so that the user's sleeping posture may be adjusted.

However, the existing electric beds can only reduce the risk of snoring on snorer, but it does not help a user to understand his physical condition.

In addition, anti-snoring program of the existing electric bed is set by the manufacturer before leaving the factory, and the user cannot adjust it according to his/her situation.

In addition, the existing electric bed cannot distinguish whether the user is on the electric bed, causing the anti-snoring function to be activated at all time, and wasting power.

SUMMARY

It is to be noted that the purpose of the present application is to overcome one or more of the disadvantages that have been found in the prior art, and to provide an electric bed having an intelligent anti-snoring function capable of providing an application situation of the anti-snoring function to an intelligent terminal used by a user so that the user can grasp his/her physical condition.

For this purpose, an electric bed with an intelligent anti-snoring function is proposed according to the present application, which is realized by the following technical solutions:

In one aspect of the present application, an electric bed includes: a bed body; a plurality of bed planks, wherein, at least one head bed plank close to the head of the bed is rotatable; a driver, one end of the driver hinged to the head bed plank and another end thereof hinged to the bed body to drive the head bed plank to rotate; a monitoring module including a pressure sensor for determining a user's snoring according to a regular pressure change generated when the user is snoring; a driving module electrically connected to the monitoring module and the driver; when the monitoring module detects that the user is snoring, the driving module controls the driver to drive the head bed plank to rotate to an anti-snoring position; when the snoring weakens or stops, the driving module drives the head bed plank to restore to an initial position; a wireless communication module electrically connected to the driving module, wherein the wireless communication module is wirelessly connected to an intelligent terminal, the user sets an anti-snoring program through the intelligent terminal and the intelligent terminal transmits the anti-snoring program to the wireless communication module; and the wireless communication module sends an application situation of the anti-snoring function to the intelligent terminal.

With the above arrangement, the electric bed can analyze whether a user is snoring through the monitoring module. When the user is snoring, the driving module controls the driver to drive to rotate the head bed plank to a certain angle to alleviate the user's snoring. In addition, since the electric bed includes a wireless communication module, the application situation of the anti-snoring program of the electric bed can be transmitted to the user, so that the user can grasp his/her health condition, thereby preventing diseases.

In one embodiment of the present application, the electric bed further includes a recording module for recording the user's snoring condition and sending the snoring condition to the wireless communication module, and then the wireless communication module sending the snoring condition to the intelligent terminal to read. Since the electric bed has a memory module, when the application situation of the anti-snoring program cannot be transmitted to the intelligent terminal in real time, for example, if the intelligent terminal is not connected to the wireless communication module, the application situation of the anti-snoring program is first stored in the memory module, and then waits until it can be sent to the intelligent terminal.

In one embodiment of the present application, the electric bed further includes a sensor electrically connected to the driving module, wherein, when the sensor monitors that the user is on the bed, the monitoring module is activated; and when the sensor monitors that the user is not on the bed, the monitoring module is not activated, thereby achieving a power saving effect.

In one embodiment of the present application, the sensor is a thin film pressure sensor provided on the plurality of bed planks, thereby detecting whether a user is on the bed.

In one embodiment of the present application, the anti-snoring position is a position at which the head bed plank is raised at an angle ranged from 5° to 25° to improve the breathing angle of the user and relieve the symptoms of snoring.

Preferably, the anti-snoring position is a position at which the head bed plank is raised at an angle of 15°.

In one embodiment of the present application, the monitoring module is wiredly connected with the wireless communication module, and communicates with each other in both directions; and the wireless communication module is wiredly connected with the driving module and adopts serial communication.

In one embodiment of the present application, the electric bed further includes a learning module for recording an anti-snoring position that is most effective in relieving the user's snoring. Specifically, when the driving module controls the driver to change the angle of the head bed plank, the monitoring module still monitors the user's snoring situation in real time, and the driver fine-tunes the angle if the snoring is not improved. At the same time, the learning module is activated. When the monitoring module detects that the user's snoring is improved, parameters of the current anti-snoring position are transmitted to the learning module for learning and to be used next time.

In one embodiment of the present application, the monitoring module has a clock integrated therein for setting an activation time of the anti-snoring program.

In one embodiment of the present application, the driving module has a clock integrated therein for setting an activation time of the anti-snoring program.

With the above arrangement, the electric bed of the present application does not require a user's control. When the sensor detects the user's snoring, it automatically sends a command to the electric bed to drive the electric bed to move to the anti-snoring position, and automatically sends a command to the electric bed to adjust to a flat position when the snoring symptoms weaken or stop. Moreover, the electric bed can feed back the application situation of the anti-snoring program to the user's intelligent terminal through the wireless communication module, so that the user can grasp his/her health condition. Moreover, the electric bed can also have additional modules such as a recording module, a sensor and a learning module, which increase the intelligence degree of the electric bed, and further overcomes the shortage of the existing electric beds having anti-snoring function.

BRIEF DESCRIPTION OF THE DRAWINGS

It should be understood that in the present application, all features, modifications, and/or embodiments may be combined in various combinations, except in the cases of obvious contradictions and incompatibilities.

By reading the following non-limiting illustrative embodiments, and in conjunction with the drawings, other features and advantages of the present application will become apparent. In the figures.

DETAILED DESCRIPTION

Figure 1:
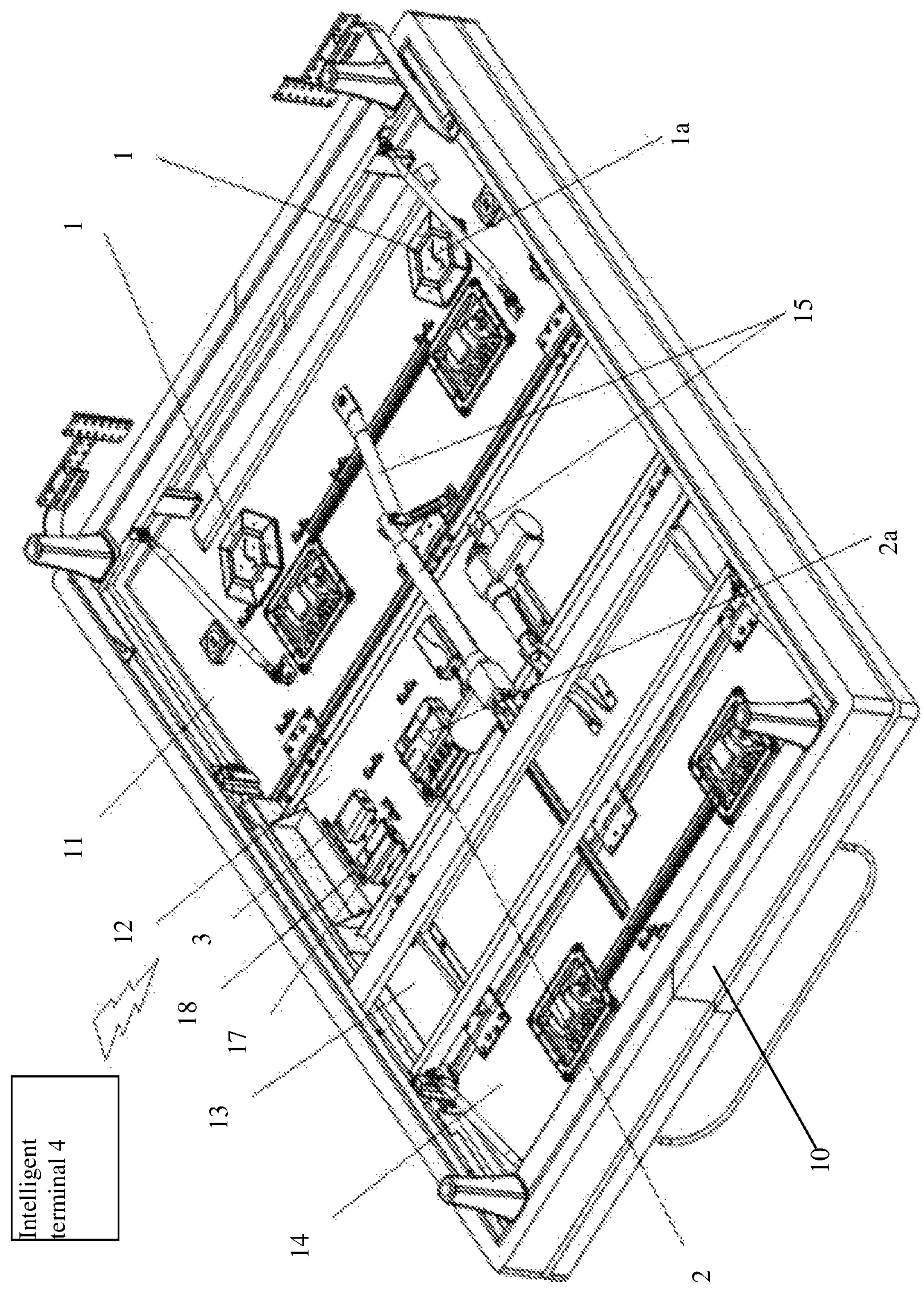
FIG. 1 is a schematic structural view showing an electric bed having an intelligent anti-snoring function according to the present application.

It should be understood that the abovementioned drawings are not drawn to actual scale, but are merely schematic representations of various preferred features for illustrating the basic principles of the present application. The design features disclosed in the present application, such as size, orientation, position, and shape, are determined based on specific applications and use environments.

The present application will be described in detail below with reference to the embodiments and the accompanying drawings. In these figures, the same reference numerals are used to refer to the same or equivalent elements of the present application in the drawings.

Figure 3:
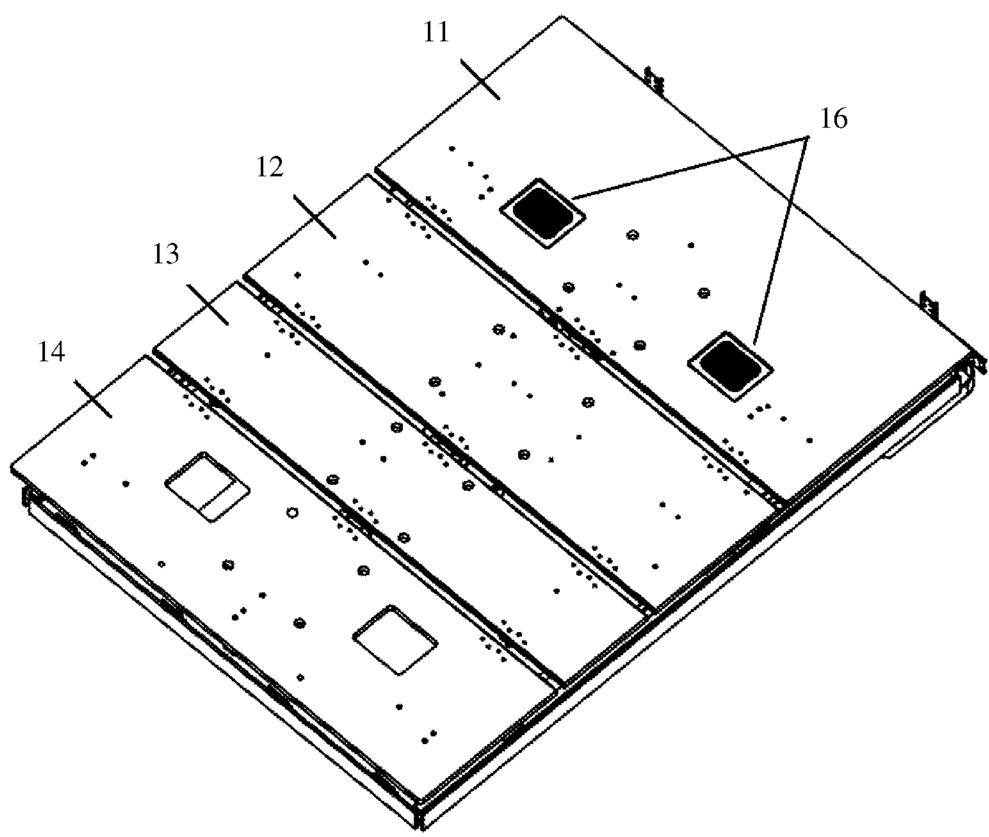
FIG. 3 is a schematic structural view showing an electric bed having a plurality of bed planks according to the present application.
Figure 4:
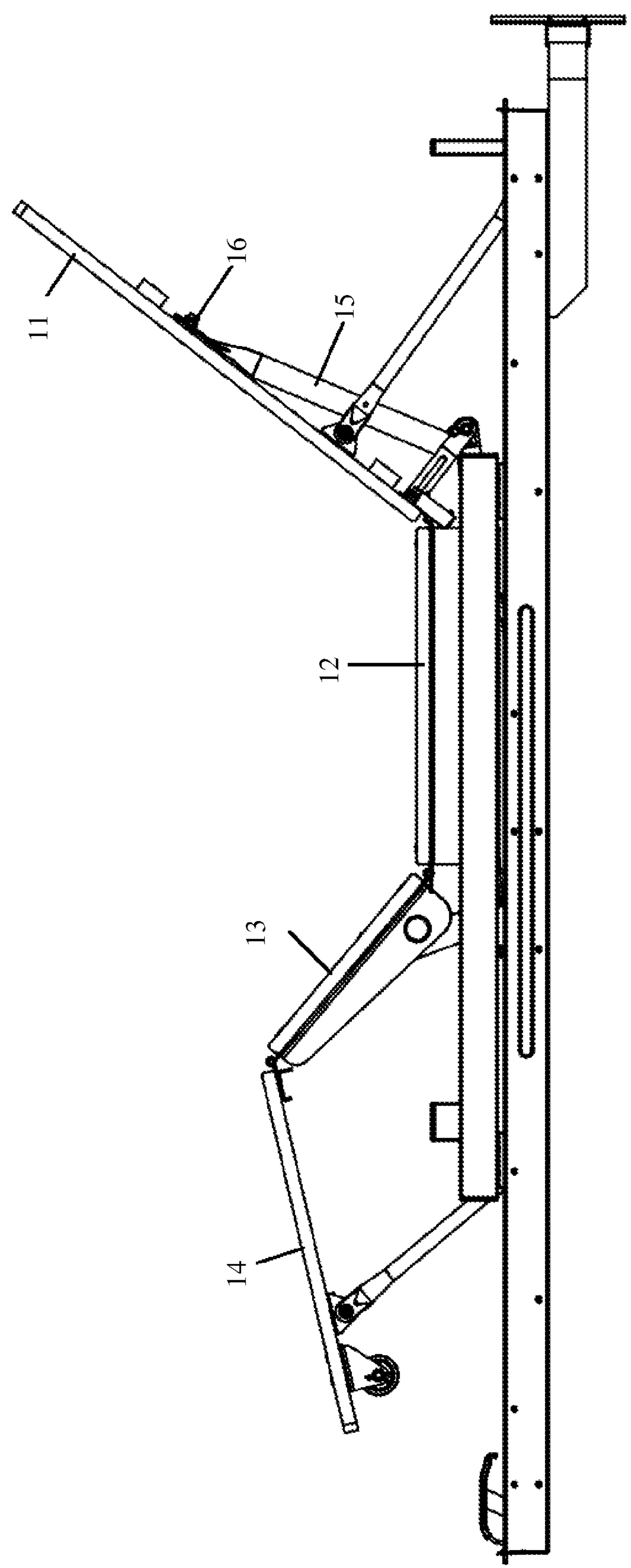
FIG. 4 is a plan view showing an electric bed having a plurality of bed planks according to the present application.

Referring to FIGS. 1 and 3-4, an electric bed in accordance with an embodiment of the present application is illustrated. The electric bed includes a bed body 10 and a plurality of bed planks. These bed planks include at least a head bed plank 11, a waist bed plank 12, a leg bed plank 13 and a foot bed plank 14. The bed planks are hinged to each other by hinges. A driver 15 for driving the head bed plank to rotate and a linkage mechanism for working with the driver are provided below the head bed plank, respectively. When the head bed plank 11 is rotated, the linkage mechanism guides the head bed plank moving in its predetermined stroke and supports the head bed plank after it moves into position, thereby ensuring that the rotation of the bed plank is reliable and that a user lying on the bed plank after rotating in place is safe.

The electric bed further includes a monitoring module 1 and a driving module 2. The driving module is electrically connected to the driver and the monitoring module so that operation of the driver can be controlled according to an anti-snoring program. Wherein, the head bed plank may be raised at an angle ranged from 5° to 25°, preferably 15°, which is set by the anti-snoring program, as shown in FIG. 4.

In addition, a thin film pressure sensor 16 is also provided on the bed planks of the electric bed. Preferably, the thin film pressure sensor is provided on each of the bed planks. The thin film pressure sensor is electrically connected to the driving module, and monitored pressure value is input into the driving module in real time, so that the driving module determines whether the user has left the bed. The driving module is configured such that when the thin film pressure sensor detects that the user has not left the bed, it allows the driving module to activate the anti-snoring program, and when the thin film pressure sensor detects that the user has left the bed, it does not allow the driving module to activate the anti-snoring program.

The electric bed further includes a wireless communication module 3 electrically connected to the driving module. The wireless communication module is adapted to be connected with an external intelligent terminal 4 by means of wireless connection, such as Wi-Fi, Bluetooth, infrared, ZigBee, 2G, 3G, 4G, or the Internet. The user sets and transmits an anti-snoring program to the wireless communication module of the electric bed through the intelligent terminal, and then the wireless communication module transmits the anti-snoring program sent by the intelligent terminal to the driving module, so that the driving module controls the driver according to the set program.

Typically, as shown in FIG. 4, the head bed plank 11 can be raised at an angle and a height, which can be set up by the intelligent terminal during a user's snoring.

Specifically, the monitoring module includes a pressure sensor for determining the user's snoring according to a regular pressure change generated when the user is snoring. The monitoring module is electrically connected to the driving module. The driving module controls the driver to raise the head bed plank at the predetermined angle when the user is snoring according to a predetermined program. The angle of the user's head is changed to reduce the symptoms of snoring. Wherein, the anti-snoring method mainly includes rotating the head bed plank to a certain angle or raising the head bed plank to a certain height to help air at the user's throat flow more smoothly, as shown in FIG. 4.

In the present embodiment, the monitoring module is wiredly connected to the wireless communication module and communicates with each other in both directions.

The wireless communication module is a Wi-Fi module, and, depending on cases, may also be a Bluetooth module, an infrared module, a ZigBee module, a 2G module, a 3G module, a 4G module, or an Internet networking module, etc., in order to wirelessly connect with the intelligent terminal. The wireless communication module is adapted to receive a control signal sent by the intelligent terminal and forward it to the driving module to determine the operation to be performed by the driving module.

Optionally, the wireless communication module feeds back the status information of the driving module back to the intelligent terminal. The wireless communication module is wiredly connected with the driving module and adopts serial communication.

The intelligent terminal includes a mobile phone, a tablet computer, a notebook computer, etc. The intelligent terminal is installed with an application (APP) and/or software for controlling the electric bed. Using the installed application (App) and/or software, the intelligent terminal controls a wireless module inside the intelligent terminal to transmit a control signal carrying a command. Both the type of the wireless module of the intelligent terminal and the type of the wireless communication module of the electric bed are a Wi-Fi module, and, depending on cases, may also be a Bluetooth module, an infrared module, a ZigBee module, or the like. Such application (App) and/or software include a human-computer interaction interface, on the one hand including a control command option interface for user's selection, and on the other hand a display interface that provides the user a first measured value information. The user can select/set functions to be controlled by clicking, double clicking, sliding, touching, and inputting values.

The head bed plank can be raised at an angle and a height, which can be set up in the intelligent terminal by the user.

Alternatively, the electric bed further includes a recording module 17. The recording module is electrically connected with the monitoring module and the driving module. The recording module is configured for recording whether the monitoring module and the driving module work in coordination, and also recording the user's sleeping state. Specifically, clocks 1*a* and 2*a* may be integrated into the monitoring module 1 and the driving module 2 for respectively recording a working state at each time. Additionally, the recording module may be electrically connected with the wireless communication module so that the recording data can be transmitted to the intelligent terminal so that the user can understand his/her sleeping state.

Alternatively, the electric bed further includes a learning module 18. The learning module is electrically connected with the monitoring module and the driving module. The learning module is configured for recording the rotated angle and raised height of the head bed plank that are most effectively in relieving the user's snoring symptoms, and during the process, the learning module can gradually learn a more effective angular position to improve the user's sleep quality. Specifically, clocks are integrated into the monitoring module and the driving module for respectively recording the user's snoring condition and the rotated angle and raised height of the head bed plank at each time. When the snoring is not be relieved during a period of time, the driving module drives the driver to finely adjust the rotated angle and the raised height of the head bed plank so that a rotated angle and raised height that are most effective in relieving the user's snoring can be obtained.

Figure 2:
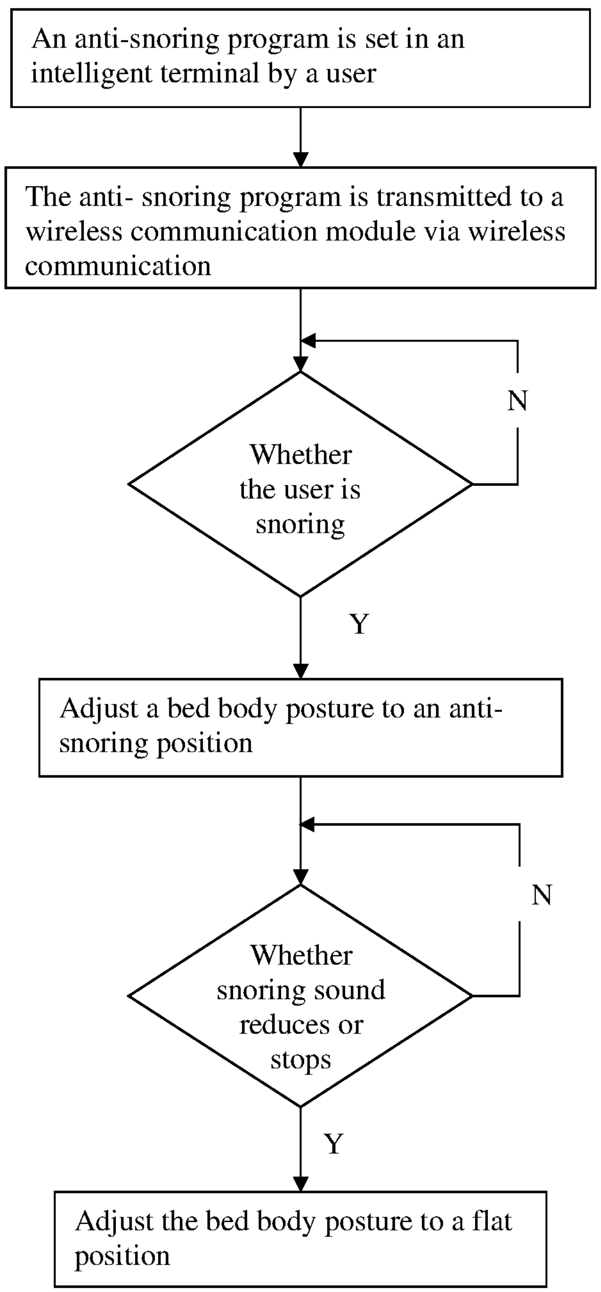
FIG. 2 is a flow chart showing the operation of the intelligent anti-snoring function of FIG. 1.

As shown in FIG. 2, a flow chart of working steps of the electric bed of the present application when performing the intelligent anti-snoring function is shown.

Step 1: an anti-snoring program is set in the intelligent terminal by the user;

Step 2: the intelligent terminal transmits the anti-snoring program to the wireless communication module by means of wireless communication;

Step 3: when the monitoring module detects that the user is snoring, the bed body is adjusted to the anti-snoring position according to the user's setting; and Step 4: when the snoring symptoms weaken or stop, the bed body is adjusted to a flat position.

The above embodiments are merely examples and do not limit the scope of the present application. Based on this, those skilled in the art can envision other embodiments that can achieve the same function within the scope of the claims of the present application.

Various embodiments and various modifications and improvements will be apparent to those skilled in the art. In particular, it should be understood that the above-described features, modifications, and/or embodiments of the present application may be combined with each other, except in the case of obvious contradictions or incompatibilities. All of these embodiments, as well as variations and modifications, are within the scope of the present application.

What is claimed is:

1. An electric bed, comprising:

a bed body;

a plurality of bed planks, wherein, at least one head bed plank on a head side of the bed is rotatable;

a driver, one end of the driver hinged to the head bed plank and another end thereof hinged to the bed body to drive the head bed plank to rotate;

a monitoring module comprising a pressure sensor for determining a user's snoring according to a regular pressure change generated when the user is snoring;

a driving module electrically connected to the monitoring module and the driver, when the monitoring module detects that the user is snoring, the driving module controls the driver to drive the head bed plank to rotate to an anti-snoring position; when the snoring weakens or stops, the driving module drives the head bed plank to restore to an initial position;

a wireless communication module electrically connected to the driving module, wherein the wireless communication module is wirelessly connected to an intelligent terminal, the user set an anti-snoring program through the intelligent terminal and the intelligent terminal transmits the anti-snoring program to the wireless communication module; and the wireless communication module sends an application situation of the anti-snoring function to the intelligent terminal;

wherein the electric bed further comprises a sensor electrically connected to the driving module, wherein, when the sensor monitors that the user is on the bed, the monitoring module is activated; and when the sensor monitors that the user is not on the bed, the monitoring module is not activated; and wherein the sensor is a thin film pressure sensor provided on the plurality of bed planks.

2. The electric bed according to claim 1, wherein the electric bed further comprises a recording module for recording the user's snoring condition and sending the snoring condition to the wireless communication module, and then the wireless communication module sending the snoring condition to the intelligent terminal to read.

3. The electric bed according to claim 1, wherein the anti-snoring position is a position at which the head bed plank is raised at an angle ranged from 5° to 25°.

4. The electric bed according to claim 3, wherein the anti-snoring position is a position at which the head bed plank is raised at an angle of 15°.

5. The electric bed according to claim 1, wherein the monitoring module is wiredly connected with the wireless communication module, communicates with each other in both directions; and the wireless communication module is wiredly connected with the driving module and adopts serial communication.

6. The electric bed according to claim 1, wherein the electric bed further comprises a learning module for recording an anti-snoring position.

7. The electric bed according to claim 1, wherein the monitoring module has a clock integrated therein.

8. The electric bed according to claim 1, wherein, the driving module has a clock integrated therein.

* * * * *